US008168242B2

(12) United States Patent
Henderson et al.

(10) Patent No.: US 8,168,242 B2
(45) Date of Patent: May 1, 2012

(54) SITU FRUCTOOLIGOSACCHARIDE PRODUCTION AND SUCROSE REDUCTION

(75) Inventors: Wayne E. Henderson, Roscoe, IL (US); William King, Walnut Creek, CA (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 118 days.

(21) Appl. No.: 12/084,534

(22) PCT Filed: Nov. 17, 2006

(86) PCT No.: PCT/US2006/044813
§ 371 (c)(1),
(2), (4) Date: Oct. 15, 2009

(87) PCT Pub. No.: WO2007/061918
PCT Pub. Date: May 31, 2007

(65) Prior Publication Data
US 2010/0040728 A1    Feb. 18, 2010

(51) Int. Cl.
*A23L 2/02* (2006.01)
(52) U.S. Cl. .................. 426/10; 426/48; 426/599
(58) Field of Classification Search .............. 426/10, 426/48, 599
See application file for complete search history.

(56) References Cited

U.S. PATENT DOCUMENTS

| | | | |
|---|---|---|---|
| 3,826,714 | A | 7/1974 | Hasegawa et al. |
| 4,276,379 | A | 6/1981 | Heady |
| 4,308,349 | A | 12/1981 | Foley et al. |
| 4,567,142 | A | 1/1986 | Lloyd |
| 4,699,882 | A | 10/1987 | Visuri |
| 4,996,062 | A | 2/1991 | Lehtonen et al. |
| 5,120,650 | A | 6/1992 | Visuri |

FOREIGN PATENT DOCUMENTS

| | | |
|---|---|---|
| EP | 0 307 158 A2 | 3/1989 |
| JP | 04 229186 A | 8/1992 |
| JP | 08 173109 A | 7/1996 |
| JP | 08-173109 * | 9/1996 |
| WO | WO 02/083741 A2 | 10/2002 |

OTHER PUBLICATIONS

JP-08-173109-Machine Translation.*
Yun, J. W. et al. 1993. The production of high-content fructo-oligosaccharides from sucrose by the mixed enzyme system of fructosyltransferase and glucose oxidase. Biotechnol. Letters. 15 (6): 573-576.*
U.S. Appl. No. 09/990,385, filed Dec. 19, 2002, Yanai et al.
Antrim, R.L. et al. "Glucose Isomerase Production of High-Fructose Syrups." In *Applied Biochemistry and Bioengineering*, edited by L.B. Wingard Jr. et al., vol. 2: Enzyme Technology: pp. 97-155. New York: Academic Press, 1979.
Aslanidis, C. et al. "Nucleotide sequences and operon structure of plasmid-borne genes mediating uptake and utilization of raffinose in *Escherichia coli.*" *J. Bacterial.* 171(12): 6753-6763, Dec. 1, 1989.
Boddy, L.M. et al. "Purification and characterisation of an *Aspergillus niger* invertase and its DNA sequence." *Current Genetics* 24(1): 60-66, Jul. 1, 1993.
Chen, W.P. "Glucose Isomerase." *Process Biochemistry* 15(5): 30-35, 1980.
Fouet, A. et al. "Nucleotide sequence of the sucrase gene of *Bacillus subtilis.*" *Gene* 45(2): 221-5, 1986.
Hang, Y.D. et al. "Fructosyltransferase activity of commercial enzyme preparations used in fruit juice processing." *Biotechnology Letters* 17(7): 741-744, Jul. 1, 1995.
Hang, Y.D. et al. "Optimization of Enzymatic Production of Fructo-oligosaccharides from Sucrose." *Lebensmittel-Wissenschaft und -Technologie* 29(5-6): 578-580, 1996.
Hayashi, S. et al. "Immobilization of a fructosyl-transferring enzyme from *Aureobasidium* sp. on Shirasu porous glass." *Journal of Fermentation and Bioengineering* 72(1): 68-70, 1991.
Hayashi, S. et al. "Continous production of 1-kestose by β-fructofuranosidase immobilized onshirasu porous glass." *Biotechnology Letters* 13(6): 395-398, Jun. 1, 1991.
Henry, R.J. et al. "Sucrose: sucrose fructosyltransferase and fructan: fructan fructosyltransferase from *Allium cepa.*" *Phytochemistry* 19(6): 1017-1020, 1980.
Hidaka, H. et al. "A fructooligosaccharide-producing enzyme from *Aspergillus niger* ATCC 20611." *Agricultural and Biological Chemistry* 52(5): 1181-1187, 1988.
Hirayama, M. et al. "Purification and Properties of a Fructooligosaccharide-producing β-Fructofuranosidase from *Aspergillus niger* ATCC 20611." *Agric. Biol. Chem* 53(3): 667-673, 1989.
Lüscher, M. et al. "Cloning and Functional Analysis of Sucrose:Sucrose 1-Fructosyltransferase from Tall Fescue." *Plant Physiol.* 124(3): 1217-1227, Nov. 1, 2000.
Sato, Y. et al. "Sequence analysis of the *Streptococcus mutans* scrB gene." *Infect. Immun.* 56(8): 1956- 1960, Aug. 1, 1988.
Su, Y.-C. et al. "Recovery and properties of a fructooligosaccharides-producing beta-fructofuranosidase from *Aspergillus japonicus* CCRC 38011." *Proc Natl Sci Counc Repub China B* 17(2): 62-9, Apr. 1993.
Unger, C. et al. "cDNA Cloning of Carrot (*Daucus carota*) Soluble Acid β-Fructofuranosidases and Comparison with the Cell Wall Isoenzyme." *Plant Physiol.* 104(4): 1351-1357, Apr. 1, 1994.
Yun, J.W. et al. "Separation and purification of fructo-oligosaccharides by an ion-exchange resin column." *Korean Journal of Biotechnology and Bioengineering* 9(1): 35-39, 1994.
PCT search document for PCT/US2006/044813.

* cited by examiner

*Primary Examiner* — D. Lawrence Tarazano
*Assistant Examiner* — Hamid R Badr
(74) *Attorney, Agent, or Firm* — Danisco US Inc.

(57) ABSTRACT

The invention pertains to an in situ process for producing fructooligosaccharides in a food product by contacting the food product with a fructosyltransferase to enzymatically convert sucrose to fructooligosaccharides in the food product. The increase in fructooligosaccharides results in an increase in dietary fiber content of the food product.

8 Claims, 2 Drawing Sheets

SITU FRUCTOOLIGOSACCHARIDE PRODUCTION AND SUCROSE REDUCTION

FIELD OF THE INVENTION

The present invention relates to an in situ process for simultaneously reducing endogenous sucrose levels in food products while elevating the levels of soluble dietary fiber. More specifically, the process relates to an enzymatic process for producing fructooligosaccharides in a food product by contacting a food product containing naturally occurring sucrose with a fructosyltransferase. The invention further relates to a high-fiber food product, produced by the process according to the invention, said food product including fructooligosaccharides.

BACKGROUND OF THE INVENTION

In recent years, numerous studies have shown the negative health effects of high consumption of simple sugars and the positive health benefits of increasing the soluble dietary fiber in human diets. In response to these studies and the popularity of certain diets that emphasize the reduction of glycemic load, consumers demand lower glycemic index foods, which are less sugary and higher in soluble dietary fiber. To meet this demand, the food industry has given particular attention to a number of substitutes for the traditional sugary carbohydrates. These include non-nutritive sweeteners, sugar alcohols, isomaltooligosaccharides and fructooligosaccharides. Particular interest has been directed to the fructooligosaccharides (FOSs). These compounds impart mild sweetness, but also significantly, they are soluble dietary fibers with documented health benefits. FOSs are found naturally in, for example, banana, tomato, onion and numerous other plant sources. For commercial use, FOSs are produced enzymatically from sucrose using fructosyltransferase enzymes. FOSs are commercially available as a nutritional supplement and have Generally Recognized As Safe (GRAS) status. While publications exist on the use of FOS as a nutritional supplement, disclosed herein is a novel in situ process to convert endogenous or naturally occurring sucrose in a food product to a soluble dietary fiber (e.g., FOS) by contacting the food product with a fructosyltransferase.

SUMMARY OF THE INVENTION

In a first aspect, the invention relates to an in situ process for producing fructooligosaccharides (FOSs) in a food product by contacting the food product with a fructosyltransferase (FT) to enzymatically convert the sucrose in the food product to fructooligosaccharides. The FOS increase in the food product results in an increase in dietary fiber content.

In a second aspect, the invention relates to an in situ method of reducing the sucrose content or glycemic index of a food product and simultaneously increasing the dietary fiber content of the food product by contacting the food product with a fructosyltransferase to enzymatically convert the sucrose in the food product to fructooligosaccharides, thereby reducing the sucrose content or glycemic index of the food product as compared to a corresponding food product.

In some embodiments of the first and second aspects, the fructosyltransferase is contacted as an immobilized enzyme. Additional enzymes, that remove byproducts of the FT reaction may also be present to help drive the reaction towards completion and further reduce glycemic index, for example glucose oxidases. In other embodiments, the contacting occurs before the food product has been pasteurized. In further embodiments, the food product is a beverage such as a fruit juice.

In a third aspect, the invention relates to a high-fiber beverage produced according to the in situ method of the invention. In one embodiment of this aspect, the high-fiber beverage is a fruit drink (e.g., an orange juice drink or an apple juice drink).

DETAILED DESCRIPTION OF THE INVENTION

Figure 1A:
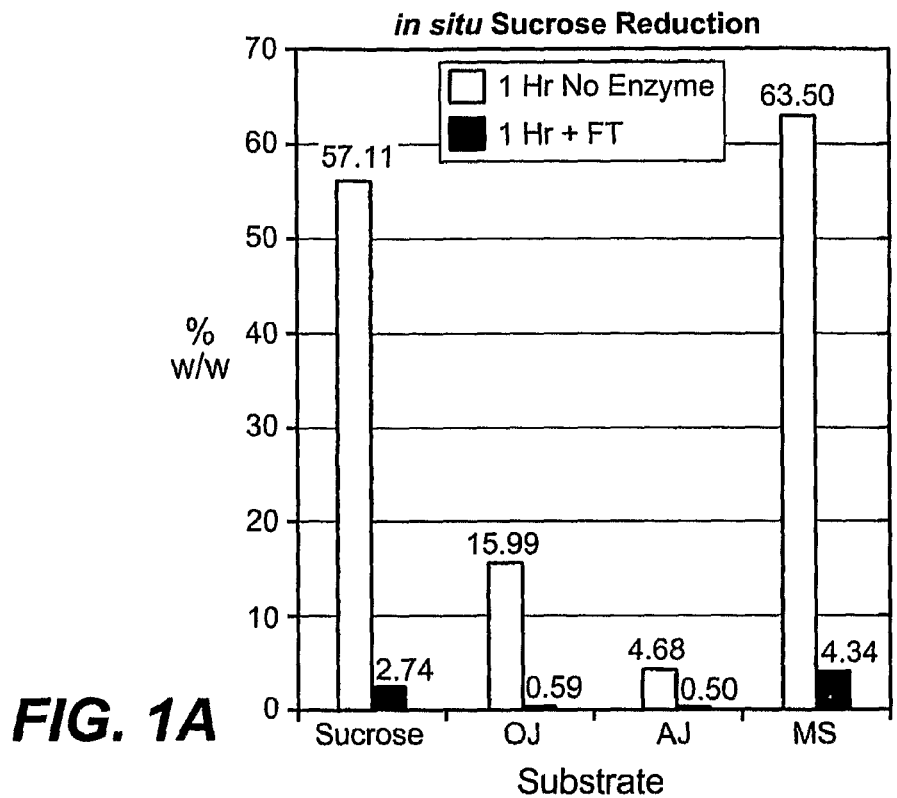
FIGS. 1A and 1B illustrate in situ sucrose reduction measured as % w/w and concurrent in situ dextrose production measured as % w/w in various substrates after 1 hour of contacting the substrates with a fructosyltransferase (FT) derived from *Aspergillus japonicus* as compared to corresponding substrates not exposed to FT. OJ refers to orange juice, AJ refers to apple juice, MS refers to maple syrup and further reference is made to Example 1.

In some aspects, the present invention relies on routine techniques and methods used in the field of industrial enzymology. The following resources include descriptions of general methodology useful in accordance with the invention: INDUSTRIAL ENZYMOLOGY, $2^{nd}$ Ed. Edited by Godfrey & West, Macmillan Press Ltd. (1996). This general reference provides definitions and methods known to those in the art. However, it is not intended that the present invention be limited to any particular methods, protocols, and reagents described, as these may vary.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, NY (1991) provide one of skill with a general dictionary of many of the terms used in this invention.

Although any methods and materials similar or equivalent to those described herein can be used in the practice or testing of the present invention, some preferred methods and materials are described.

The headings provided herein are not limitations of the various aspects or embodiments of the invention, which can be had by reference to the specification as a whole.

DEFINITIONS

The term "sucrose" means a disaccharide comprised of 1 mole of D-glucose and 1 mole of D-fructose wherein the C-1 carbon atom of the glucose and the C-2 carbon atom of the fructose participate in the glycoside linkage.

The term "endogenous" as used herein with reference to sucrose or fiber refers to sucrose or fiber that is naturally contained in a food product (native sucrose or fiber).

The term "disaccharide" as used herein refers to any compound that comprises two covalently linked monosaccharide units. The term encompasses but is not limited to such compounds as sucrose, lactose and maltose.

The term "oligosaccharide" as used herein refers to a compound having 2 to 10 monosaccharide units joined by glycosidic linkages.

As used herein the term "dextrose" is used interchangeably with the term "glucose".

The term "fructooligosaccharides (FOSs)" means short chain oligosaccharides comprised of D-fructose and D-glucose units. Some preferred FOSs are short chain molecules with no more than 6 fructose residues. For example some preferred FOSs comprise of one molecule of D-glucose in the terminal position and from 2 to 4 D-fructose units having the structural formula below wherein n=2-4 fructose residues. The linkage between fructose residues in FOSs are a beta-(2-1) glycosidic links.

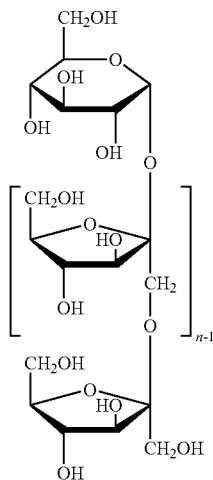

The term "fructosyltransferase (FT)" means enzymes having fructose transferase activity, which are capable of producing fructooligosaccharides in the presence of sucrose. Enzymes having fructose transferase activity have been classified as E.C. 2.4.1.99 (sucrose:sucrose fructosyltransferases) and E.C. 3.2.1.26 (beta-D-fructofuranosidases or beta-fructosidases).

The term "food product" is broadly defined as a food or beverage which is consumable and includes sucrose.

A "corresponding food product" refers to a food product that has not been contacted with a fructosyltransferase according to the process of the invention, but has otherwise been exposed to essentially the same conditions as a subject food product contacted with a fructosyltransferase according to the process of the invention.

"In situ" refers to a process wherein fructosyltransferase is directly contacted with a food product.

The term "contacting" refers to directly exposing a food product to a fructosyltransferase.

The term "substantially all converted" refers to maintenance of a low sucrose concentration in the food product.

The phrase "low sucrose concentration" or "reducing the sucrose concentration" refers to a concentration level of sucrose in a food product that is less than the concentration level of sucrose in a corresponding food product, which has not been contacted with FT according to the methods of the invention. In some embodiments, a low sucrose concentration mean essentially complete removal of the sucrose in the food product.

The term "enzymatic conversion" refers to the modification of a carbon substrate to an intermediate or the modification of the intermediate to an end product by contacting the substrate or intermediate with an enzyme.

The phrase "FOS producing reaction" means the process of contacting a food product with a fructosyltransferase to enzymatically convert sucrose to FOSs.

The phrase "a high-fiber food product" means a food product in which the level of FOS is elevated over the endogenous FOS level in the corresponding food product and obtained by the in situ process encompasses by the invention.

A "glucose isomerase" (e.g., EC 5.3.1) refers to an enzyme that isomerizes glucose, to fructose (e.g. EC 5.3.1.9).

A "glucose oxidase" (e.g., EC 1.1.3.4) refers to an enzyme that catalyzes the reaction between glucose and oxygen producing gluconate and hydrogen peroxide.

An "enzyme unit" is defined as the amount of enzyme responsible for transferring one micromole of fructose per minute under standard conditions or as the amount of enzyme for producing one micromole of glucose under standard conditions.

The term "ATCC" refers to American Type Culture Collection located at Manassas, Va. 20108 (ATCC; <www.atcc.org>).

The process according to the present invention concerns obtaining a food-product, which contains sucrose and contacting the food product with a fructosyltransferase to enzymatically produce fructooligosaccharides (FOS).

EMBODIMENTS

The food product is preferably a beverage (e.g. a sweet beverage) or a sweetener such as a syrup. Preferred beverages include fruit juices such as, orange, apple, grapefruit, grape, pineapple, cranberry, lemon, prune and lime juices. Particularly preferred beverages are orange and apple fruit juices.

Examples of syrups include maple syrup, strawberry syrup, blueberry syrup, and boysenberry syrup.

In some embodiments, a food product will have a % total solids (% DS) of about 0.1% to 80% and also about 1% to 60%. In some embodiments, when the food product is a fruit beverage the DS will range from 1 to 80%.

In some embodiments, when the food product is a natural juice (e.g. a non-concentrated juice) the % DS may range from 0.1% to 15%, also 0.5% to 10% and even 0.5% to 5%. In other embodiments, when the food product as been concentrated the % DS may range from 25% to 90%, also from 25% to 80%, also from 30% to 60% and even 35% to 50%.

Using orange juice as one specific example, the FOS producing reaction can be conducted at a solids level ranging from natural juice (e.g., about 12% w/v solids or less, such as less than 10%, less than 8% or less than 6%) to concentrated juice (e.g., about 40% w/v solids or higher, such as greater than 45%, greater than 50%, greater than 55% or greater than 60%).

The initial sucrose level will vary with the type of food product. In some embodiments, the % sucrose (w/v) in the food product will be about between 2% and 75%, also between 10% and 55%, between 25% and 55% and further between 30 and 45%. In other embodiments, the sucrose level in orange juice may be about 2 to 12%, such as 4 to 10%, while the initial sucrose level in concentrated orange juice may be about 20 to 45%, such as 25 to 40%.

Fructosyltransferases (FT) useful for the practice of the invention are classified as EC.2.4.1.99 and exhibit transferase activity. Such enzymes are sometimes also called beta-fructofuranosides. Beta-fructofuranosides also include hydrolytic enzymes classified as EC. 3.2.1.26. The term FT as used herein applies to any enzyme capable of catalyzing the transfer reaction and the use of this term in no way restricts the scope of the invention.

Fructosyltransferases may be derived from plant sources such as asparagus, sugar beet, onions, Jerusalem artichokes and others (See, Henry, R. J. et al., (1980) *Phytochem.* 19: 1017-1020; Unger, C. (1994) *Plant Physiol.* 104: 1351-1357; and Luscher, M. et al., (2000) *Plant Physiol.* 124:1217-1228).

Fructosyltransferase may also be derived from fungal sources, such as *Aspergillus, Aureobasidium* and *Fusarium*. More specific examples include *Aspergillus japonicus*, such as CCRC 38011; *Aspergillus niger*, such as ATCC 20611; *Aspergillus foetidus* (such as NRRL 337); *Aspergillus aculeatus; Aureobasidium pullulans*, such as ATCC 9348, ATCC 12535; and ATCC 15223 (See, Yuan-Chi Su et al., (1993) *Proceedings National Science Council*, ROC 17:62-69; Hirayama, M. et al., (1989) *Agric. Biol. Chem.* 53: 667-673; Hidaka, H., et al., (1988) *Agric. Biol. Chem.* 52:1181-1187; Boddy, L. M. et al., (1993) *Curr. Genet.* 24:60-66; and U.S. Pat. No. 4,276,379).

Fructosyltransferases additionally may be derived from bacterial sources, such as *Arthrobacter* (Fouet, A. (1986) *Gene* 45:221-225; Sato, Y. et al. (1989) *Infect. Immun.* 56:1956-1960; and Aslanidis, C. et al., (1989) *J. Bacteriol.*, 171: 6753-6763).

In some instances, the fructosyltransferase may be a variant of a naturally occurring fructosyltransferase. Reference is made to U.S. Pat. No. 6,566,111, wherein a beta-fructofuranosidase was genetically engineered to improve the productivity of the enzyme. Also, see Koji Y., et al., US 20020192771.

Fructosyltransferase may be obtained from commercial sources such as PECTINEX ULTRA SP-L (Novozymes A/S) and RAPIDASE TF (DSM).

The fructosyltransferase may be used in a soluble form or the enzyme may be immobilized by any number of techniques known in the art and these include adsorption on a carrier, as described for example in WO 02083741A (See, Hayashi et al., 1991 *J. Ferment. Bioeng.* 72:68-70 and Hayashi et al., (1991) *Biotechnol. Letts* 13:395-398). Immobilization of the enzyme may allow for the economic use of high enzyme dosage and eliminates or reduces the need for removal or inactivation of residual enzyme from the product. Soluble enzymes may be optionally inactivated by pasteurization or other known methods.

The amount of fructosyltransferase used in the process according to the present invention will vary depending on a number of variables. These variables include but are not limited to, the food product used in the invention process; the amount of FOS to be produced; the treatment time; the inclusion of an enzyme catalyst, such as glucose isomerase in the process; and other process conditions. One of skill in the art will readily be able to determine the amount of fructosyltransferase to be used in the process according to the invention.

Additionally as known in the art, enzyme dose and reaction time are inversely proportional, and therefore it is useful to calculate the product of dose and reaction time as a measure of the degree of reaction. For example, two hours at a dose of one unit per gram of sucrose (dose time=2 U■hrs/g) is about equal to one hour of reaction at a dose of 2 U/g (also 2 U■hrs/g).

In some embodiments, a dose time of about 0.5 U■hrs/g to 400 U■hrs/g will be required to convert sucrose to FOS. In other embodiments the dose time will be about 0.5 U■hrs/g to 200 U■hrs/g; also about 1.0 U■hrs/g to 100 U■hrs/g; and further about 1.0 U■hrs/g to 50 U■hrs/g.

While under some conditions a low dose time may be required (e.g. around 1 to 2 U■hrs/g) under other conditions a greater dose time may be required to provide the same degree of conversion. For example, when the pH of the food product is acidic, the fructosyltransferase may be less active and a greater dose time will be required. In some nonlimiting examples a dose time of about 200 U■hrs/g to or greater may be required for the enzymatic conversion by a fructosyltransferase process under acidic conditions.

The fructosyltransferase is contacted with the food-product under suitable conditions for the formation of FOSs. In some embodiments, substantially all of the sucrose of the food-product is enzymatically converted to FOSs. In other embodiments, the sucrose concentration is reduced in the food product as described below. In some embodiments, the quality of the food product, which includes e.g., texture, taste, color and odor is essentially maintained.

In some embodiments, the FOS producing reaction will proceed under a large range of temperature conditions, and this may be a function of time. In some embodiments, the temperature range is about −10° C. to 95° C., about −5° C. to 90° C., about 1° C. to 80° C., about 1° C. to 75° C.; about 1° C. to 70° C.; about 5° C. to 65° C., about 5° C. to 60° C., about 5° C. to 55° C., about 10° C. to 50° C.; about 5° C. to 40° C.; and about 10° C. to 40° C. In other embodiment the temperature range will be about −10° C. to about 10° C. In other embodiments, the FOS producing reaction will proceed under pH conditions in the range of about pH 3.0 to 8.0; about pH 3.0 to 7.0; about pH 3.0 to 6.0 and about pH 3.5 to 6.0. In some embodiments, the FOS producing reaction will proceed under pH conditions of about pH 3.0 to 4.5 for orange juice and apple juice and also about pH 5.5 to 7.5 for maple syrup.

In some embodiments, the contacting will proceed for as little as 1 minute and in other embodiments for as long as several days or weeks. In some embodiments the contacting will occur for 30 minutes to 48 hours. In some embodiments, the contacting may continue during the shipping and storage of the food product prior to consumption. In other embodiments, the sucrose is enzymatically converted to FOS in about 1 minute to 60 hours.

In some embodiments, the suitable contacting conditions may be different from the conditions considered optimum for enzyme activity, particularly to maintain organoleptic qualities, and it may be necessary to adjust time of contacting and fructosyltransferase enzyme dosage. As one non-limiting example, the activity of a fructosyltransferase that has an optimum at about pH 5.5 and about 50° C., will be slowed when contacted with a fruit beverage at about pH 3.6 and about 5° C. Time of contacting and enzyme dosage adjustments are within the skill of one in the art.

The FOS producing reaction can occur at any time during the processing of a food-product and may be allowed to continue during storage prior to consumption.

The process according to the instant invention may occur prior to, currently with or after pasteurization. In other embodiments, the FOS producing reaction will proceed under cold processing conditions, for example in a range of −5° C. to 10° C. for fruit juices.

The FOS producing reaction may be terminated by conditions leading to denaturization of the fructosyltransferase, such as heat or pasteurization at low pH or by physically removing the catalyst in the case of immobilized fructosyltransferase. For example, in processing fruit juices for consumption, the juice is generally subjected to pasteurization treatment. In some cases, this treatment may be from about 15 seconds to 60 minutes, 15 seconds to 30 minutes, 5 minutes to 25 minutes and also 10 minutes to 20 minutes at a temperature of about 60° C. to 95° C. and generally at a temperature of about 65° C. to 75° C.

The fructosyltransferase enzymatically converts sucrose into a FOS. A FOS containing 2 fructose residues is abbreviated GF2 (G is for glucose and F is for fructose). A FOS containing 3 fructose resides is abbreviated GF3 and those having 4 fructose residues are abbreviated GF4. GF2 is also known as 1-kestose, GF3 is also known as nystose.

In some embodiments, the FOS level in the food product will be increased by at least 0.5%, 1%, 5%, 10%, 15%, 20%, 25%, 30%, 40%, 50%, 75%, 80%, 85%, 90%, 95%, 100%, 200%, 300% and greater as compared to the corresponding food product. However, typically, a corresponding food product essentially does not contain FOSs or contains less than 1% (e.g., between 0 to 1.0% and 0 to 0.5%) FOSs. In some embodiments, at least 20%, 25%, 30%, 40%, 45%, 50%, 55% and 60% of the FOS produced in the food product comprises GF2. In some embodiments, the increase in the FOS level take place between 15 minutes to 62 hours (e.g., between 15 minutes and 48 hours, between 15 minutes and 36 hours, and between 30 minutes and 24 hours).

In other embodiments, between 100% and 20% of the sucrose in the food product will be enzymatically converted to FOS by the process of the invention. In some embodiments, at least 40%. at least 50%, at least 60%, and also at least 70% of the sucrose in the food-product will be converted to FOS by the process according to the invention. In some embodiments, the enzymatic conversion of sucrose to FOS will occur in the range of between 15 minutes to 62 hours (e.g., between 15 minutes and 48 hours, between 15 minutes and 36 hours and between 30 minutes and 24 hours).

In some embodiments, the sucrose level in the food product may be reduced by at least 5%, 10%, 15%, 20%, 25%, 30%, 35%, 40%, 45%, 50%, 55%, 60%, 65%, 70%, 75%, 80%, 85%, 90%, and 95% as compared to the corresponding food product. In some embodiments, the amount of sucrose will be reduced by more than 50%, and in other embodiments, the amount of sucrose will be reduced by more than 90% as compared to the corresponding food product. In some embodiments, the food product produced by a process of the invention will include about 0.5%, 1%, 2%, 5% or 10% sucrose.

In other embodiments, a method encompassed by the invention produces a food product with a dextrose (glucose) level that is at least 25%, 50%, 75%, 100%, 125% or greater than the dextrose level of the corresponding food product. In some embodiments, the glucose level of a food product contacted with a fructosyltransferase according to the invention will be between 0.1 to 20% w/v (weight/volume). In other embodiments, the initial food product may have a very low level or essentially no dextrose to begin with and the process according to the invention produces a product having essentially no dextrose. In some embodiments, the amount of fructose produced in the food product will be less than 5%, less than 2% less than 1% and also in some embodiments less than 0.5%.

In some embodiments, the production of FOS according to the methods of the invention is stable meaning that there is essentially no reversion of naturally occurring sucrose. In some embodiments, FOS, which is produced according to methods of the invention is not substantially hydrolyzed to yield glucose and fructose. In some embodiments, the in situ FOS formation may be directly correlated with dextrose production.

The enzymatic conversion of sucrose to fructooligosaccharides according to the process of the invention may be enhanced by the presence of enzymes which catalyze the conversion of glucose to other compounds such as glucose isomerases and/or glucose oxidases. Sources of these enzymes are well known.

Glucose isomerases may be obtained for example from *Bacillus, Streptomyces* and *Aerobacter* species. (See, U.S. Pat. No. 3,826,714; U.S. Pat. No. 4,308,349; U.S. Pat. No. 4,567,142; U.S. Pat. No. 4,699,882 and U.S. Pat. No. 5,120, 650). Reference is also made to Antrim et al., (1979) APPL. BIOCHEM & BIOENGINEER. V2 Academic Press and Chen et al., (1980)*Process Biochem* 30-35). Glucose oxidases may be obtained from *Aspergillus niger*. (See, U.S. Pat. No. 4,996, 062). These enzymes may also be obtained from commercial sources such as Gensweet and OxyGO® from Genencor International, Inc.

Methods well known in the art are available for determining the level of FOS in a food product. A direct method of measuring FOS is by HPLC (Yun J. W. et al., (1993). *Korean J. Biotechnol. Bioeng.* 9:35-39). Other methods include chromatography and NMR. In the absence of a hydrolytic reaction, the formation of each FOS bonds leads to the release of a glucose molecule which may be measured by a wide variety of method including the glucose oxidase based blood glucose test strips as disclosed in the examples.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

Example 1

In situ Sucrose Reduction and Dextrose Production in Various Substrate Food Products Contacted with Fructosyltransferase Derived from *Aspergillus japonicus* EB001

Samples of orange juice concentrate, apple juice concentrate, maple syrup and sucrose were obtained from a grocery store. The sucrose was dissolved to 50% ds in water. Dry substance (ds) level of each food product was determined by calculation from the refractive index, with the calculation assuming that the solids present were sucrose. Each of the four food products was adjusted to pH 5.6±0.1 and exposed to 14 fructosyltransferase U/gds or no enzyme as a control and held at 52° C. for 24 hours. Residual glucose and sucrose were determined by HPLC in samples taken during the reaction (Table 1).

Figure 1B:
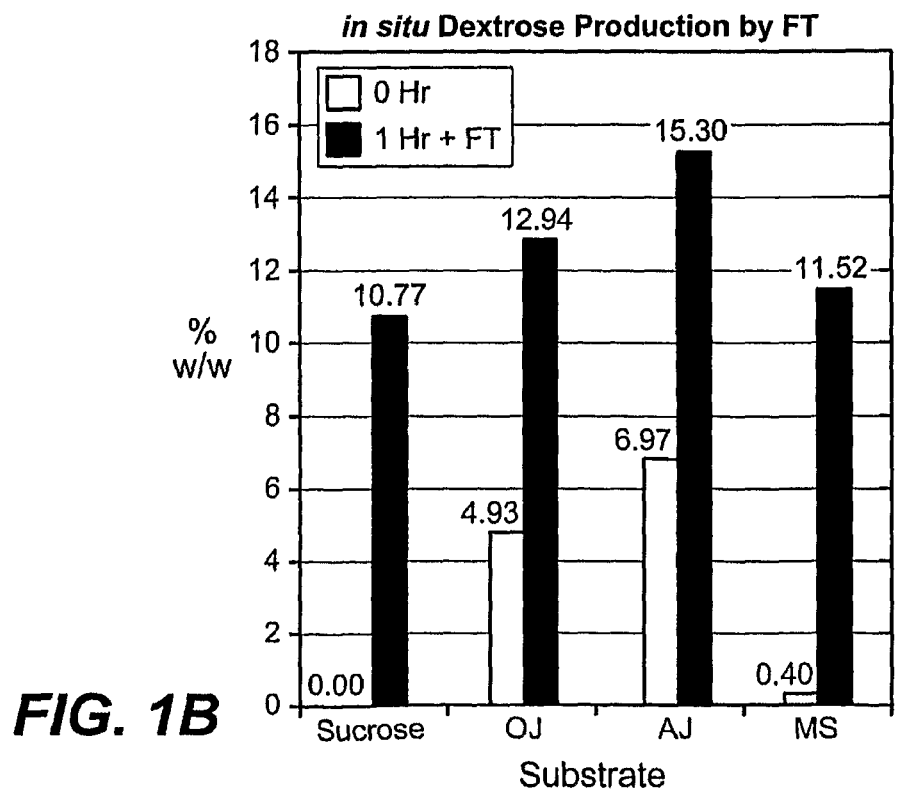

The results obtained after 1 hour and 24 hours are illustrated in Table 1 and the results obtained after 1 hour are illustrated in FIGS. 1A and 1B.

TABLE 1

|  | Sucrose −FT/+FT | Orange Juice −FT/+FT | Apple Juice −FT/+FT | Maple Syrup −FT/+FT |
|---|---|---|---|---|
| pH | 5.65 | 5.69 | 5.64 | 5.51 |
| RI | 1.42 | 1.40 | 1.40 | 1.45 |
| C | 31 | 31 | 30 | 31 |
| % ds | 50.2 | 40.6 | 40.8 | 65.6 |
| Gds | 20.1 | 16.3 | 16.3 | 26.3 |
| Mls | 0/405 | 0/325 | 0/330 | 0/525 |
| U/gds | 0/14.24 | 0/14.13 | 0/14.28 | 0/14.14 |

TABLE 1-continued

|  | Sucrose −FT/+FT | Orange Juice −FT/+FT | Apple Juice −FT/+FT | Maple Syrup −FT/+FT |
|---|---|---|---|---|
| Sucrose Reduction % w/w, 1 hr | 57.11/2.74 | 15.99/0.59 | 4.68/0.50 | 63.50/4.43 |
| Sucrose Reduction % w/w, 24 hr | 66.25/2.05 | 16.07/0.64 | 5.01/0.42 | 66.40/2.88 |
| Dextrose Production % w/w, 1 hr | 0.0/10.77 | 4.46/12.94 | 6.85/15.30 | 0.37/11.52 |
| Dextrose Production % w/w, 24 hr | 0.03/13.79 | 5.16/14.71 | 7.24/13.05 | 0.31/19.24 |

Sucrose = Crystal (United Sugar Corp., Minneapolis, MN); Orange Juice = Minute Made pulp free (Coca Cola, Houston, TX); Apple Juice = Seneca (NCI Foods Corp., Wisconsin Rapids, WI); and Maple Syrup = Grade A dark amber (Maple Grove Farms of Vt, Inc. St. Johnsbury, VT).

Table 1 and FIGS. 1A and 1B illustrate there was little or no change in composition of the four substrates over 24 hours (hrs) of incubation in the absence of FT. Removal of sucrose is observed from all four substrate samples in the presence of the FT. The loss of sucrose from the substrates was associated with an increase in dextrose and no increase in fructose.

Example 2

In Situ Sucrose Reduction and Dextrose Production in a Sucrose Solution at pH 3.5 Contacted with Fructosyltransferase Derived from *Aspergillus japonicus*

Figure 2:
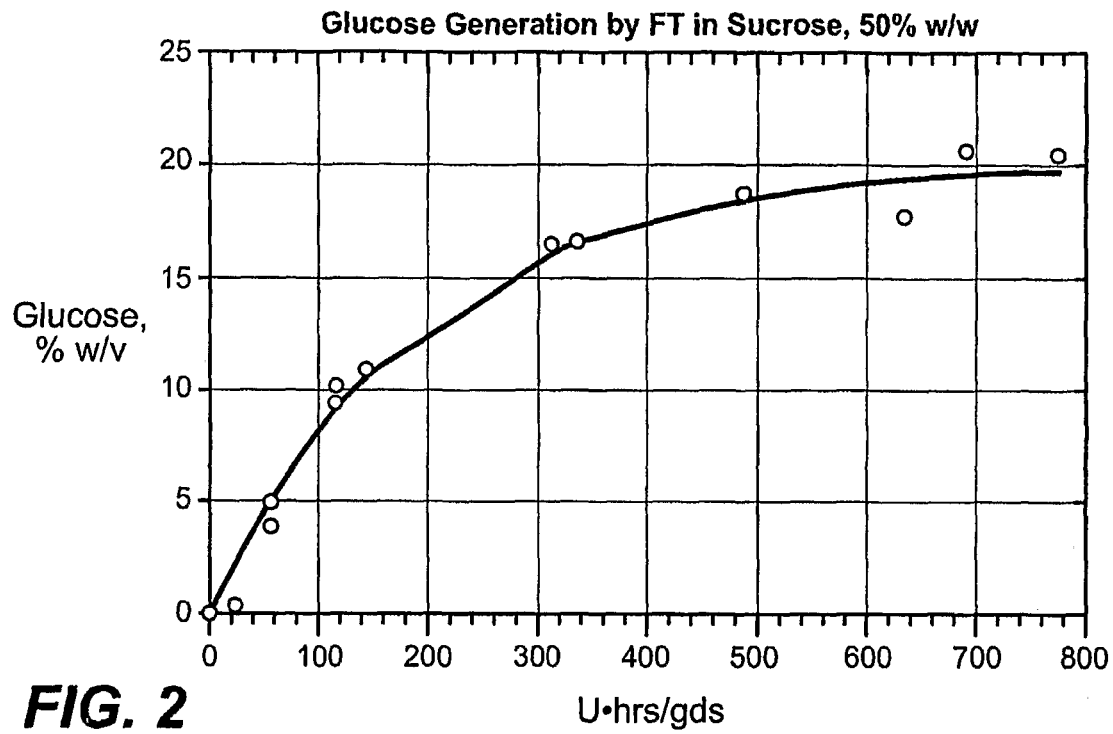
FIG. 2 illustrates in situ dextrose production, indicating the formation of FOS from sucrose at room temperature and at pH 3.5.

The 50% ds sucrose solution of example 1 was adjusted to pH 3.5 and exposed to 14 U/g ds of fructosyltransferase and held at 25° C. for 55 hours. Samples were withdrawn during the reaction and the glucose level determined using a commercially available glucose oxidase based blood glucose meter (Bayer Glucometer Elite XL with Ascensia Elite™M Blood Glucose Test Strips). The results are illustrated in FIG. 2.

Example 3

In Situ Sucrose Reduction and Dextrose Production in a Sucrose Solution Contacted at 1° C. with Fructosyltransferase Derived from *Aspergillus Japonicus*

Figure 3:
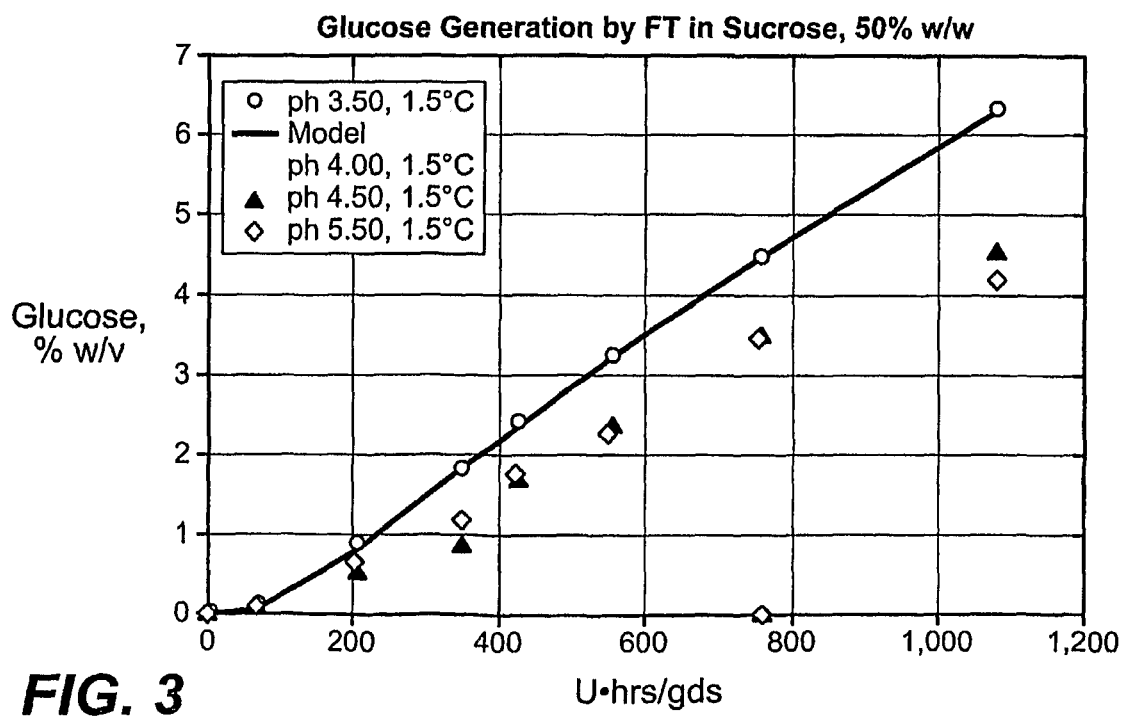
FIG. 3 illustrates in situ dextrose production, indicating the formation of FOS from sucrose at pH 4.0, 4.5 and 5.5 at a temperature of about 1.5° C.

The 50% ds sucrose solution of example 1 was adjusted to pH 3.5, 4.0, 4.5 and 5.5 with HCl and exposed to 14 U/gds of fructosyltransferase and held at 1.5° C.±0.5 C for 77 hours. Samples were withdrawn during the reaction and the glucose level determined using a commercially available glucose oxidase based blood glucose meter. The results are illustrated in FIG. 3.

Example 4

A 56% w/v sucrose solution of about 46.4% ds was contacted with fructosyltransferase (EB001) at a dosage of 5 U/gds, a temperature of 25° C. and pH 5.5. Samples were taken after 0.0, 4.0, 9.5, 21.0 and 24.0 hours of reaction time and analyzed by HPLC to determine the carbohydrate profile. Results as illustrated in Table 2 support the formation of fructooligosaccharides from fructosyltransferase activity. An absence of invertase activity is indicated by the low amount of free fructose.

TABLE 2

| Time (hrs) | U-hrs/ gds | % Sucrose | % Dextrose | % Fructose | % GF2 | % GF3 | % GF4 |
|---|---|---|---|---|---|---|---|
| 0 | 0 | 97.70 | 0 | 0 | 0 | 0 | 0 |
| 4.0 | 20 | 33.88 | 21.30 | 0.80 | 35.90 | 5.44 | 0 |
| 9.5 | 47 | 13.16 | 24.59 | 1.41 | 41.84 | 15.70 | 0 |
| 21.0 | 105 | 9.17 | 27.53 | 1.67 | 31.13 | 24.86 | 2.30 |
| 24.0 | 120 | 9.07 | 27.49 | 1.75 | 28.71 | 26.03 | 2.63 |

It is claimed:

1. An in situ process for producing fructooligosaccharides in a food product consisting essentially of contacting the food product with an enzyme composition containing only a fructosyltransferase from *Aspergillus japonicus* to enzymatically convert sucrose in the food product to fructooligosaccharides (FOSs), wherein said sucrose content of the food product is reduced by (a) at least 75% after a 1 hour exposure or (b) at least 90% after a 24 hr exposure to the fructosyltransferase as compared to a food product not treated with the fructosyltransferase.

2. The process according to claim 1, wherein at least 30% of the FOSs is comprised of 1-kestose.

3. The process according to claim 1, wherein the dextrose content of the food product is increased compared to a corresponding food product not treated with the fructosyltransferase.

4. The process according to claim 1, wherein said sucrose content of the food product is reduced by at least 75% after a 1 hour exposure to the fructosyltransferase.

5. The process according to claim 1, wherein said sucrose content of the food product is reduced by at least 90% after a 24 hr exposure to the fructosyltransferase.

6. The process according to claim 1 wherein the food product is a fruit juice.

7. The process according to claim 6, wherein the fruit juice is orange juice.

8. The process according to claim 7, wherein the orange juice is a concentrated product.

* * * * *